(12) United States Patent
Morman et al.

(10) Patent No.: US 8,034,440 B2
(45) Date of Patent: Oct. 11, 2011

(54) ELASTOMERIC FILM AND LAMINATES THEREOF

(75) Inventors: Michael Tod Morman, Alpharetta, GA (US); Prasad Shrikrishna Potnis, Duluth, GA (US); David Michael Matela, Alpharetta, GA (US); Sjon-Paul Lee Conyer, Westmoreland, TN (US); Gregory Tod Sudduth, Cumming, GA (US); Randall James Palmer, Acworth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1045 days.

(21) Appl. No.: 10/285,288

(22) Filed: Oct. 31, 2002

(65) Prior Publication Data
US 2004/0087235 A1 May 6, 2004

(51) Int. Cl.
*B32B 7/02* (2006.01)
(52) U.S. Cl. ........ 428/218; 428/219; 442/328; 442/329; 442/398; 442/399
(58) Field of Classification Search .......... 442/381, 442/394, 328, 329, 398, 399; 428/218, 219
See application file for complete search history.

(56) References Cited

U.S. PATENT DOCUMENTS

| | | | |
|---|---|---|---|
| 3,060,136 A * | 10/1962 | Nelson et al. ............. 521/150 |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,100,324 A | 7/1978 | Anderson et al. | |
| 4,340,563 A | 7/1982 | Appel et al. | |
| 4,663,220 A | 5/1987 | Wisneski et al. | |
| 4,965,122 A | 10/1990 | Morman | |
| 5,064,802 A | 11/1991 | Stevens et al. | |
| 5,114,781 A | 5/1992 | Morman | |
| 5,116,662 A | 5/1992 | Morman | |
| 5,336,545 A | 8/1994 | Morman | |
| 5,374,696 A | 12/1994 | Rosen et al. | |
| 5,418,045 A | 5/1995 | Pike et al. | |
| 5,523,136 A | 6/1996 | Fischer et al. | |

(Continued)

FOREIGN PATENT DOCUMENTS
FR 2 705 053 11/1994
(Continued)

OTHER PUBLICATIONS

Partial Machine translation of JP 08058043A.*

*Primary Examiner* — Elizabeth Cole
(74) *Attorney, Agent, or Firm* — Dority & Manning, P.A.

(57) ABSTRACT

An elastomeric film includes a first layer co-extruded with a second layer. The first layer includes a single-site catalyzed ethylene-alpha olefin copolymer having a density of about 0.860 to about 0.900 grams per centimeter. The second layer includes a styrene copolymer selected from styrene-butadiene-styrene, styrene-isoprene-styrene, styrene-ethylene/butylene-styrene, styrene-ethylene/propylene-styrene, or styrene-(ethylene/propylene)-styrene-(ethylene/propylene).
The first layer may optionally include filler particles. An extensible laminate including the elastomeric film is also disclosed.

29 Claims, 6 Drawing Sheets

U.S. PATENT DOCUMENTS

| | | |
|---|---|---|
| 6,027,776 A | 2/2000 | Mueller |
| 6,045,900 A * | 4/2000 | Haffner et al. .............. 428/315.9 |
| 6,479,154 B1 * | 11/2002 | Walton et al. ............... 428/424.4 |
| 6,638,636 B2 * | 10/2003 | Tucker .......................... 428/515 |
| 6,663,611 B2 * | 12/2003 | Blaney et al. ............ 604/385.01 |
| 6,783,842 B2 * | 8/2004 | Niepelt ......................... 428/213 |

FOREIGN PATENT DOCUMENTS

| | | |
|---|---|---|
| JP | 08058043 A * | 3/1996 |
| WO | WO 98/29480 | 7/1998 |
| WO | WO 99/33650 | 7/1999 |
| WO | WO 01/32116 | 5/2001 |
| WO | WO 01/32403 | 5/2001 |
| WO | WO 02/34512 | 5/2002 |

* cited by examiner

ELASTOMERIC FILM AND LAMINATES THEREOF

FIELD OF INVENTION

The present invention relates to elastomeric films and laminates containing them. The elastomeric films are formed by the co-extrusion of an elastomeric copolymer with a less elastic material.

BACKGROUND OF THE INVENTION

Elastomeric polymer films have found widespread use in a number of applications because of the desirable elongation and retraction properties they exhibit. For example, elastomeric films have been laminated to inelastic materials such as nonwoven webs to form elastic composites that are used in garment materials, pads, diapers, training pants, swimwear, adult incontinence products and feminine care products. One class of elastomeric polymers often chosen for use in these applications includes styrene copolymers. However, these elastomeric polymers, in their pure form, are expensive and are only available from a limited number of suppliers. In order to reduce costs while retaining the desired level of elasticity, many manufacturers have resorted to using elastomeric films including blends of elastomeric polymer with other less expensive and/or less elastic materials.

Typically, these blended elastomeric films are formed through dry blending the elastomeric polymers with the less expensive and/or less elastic materials prior to extruding, blowing or casting the film. An example of an elastomeric polymer dry-blended with a less elastic material is disclosed in, for example, commonly assigned U.S. Pat. No. 4,663,220 to Wisneski et al., which is hereby incorporated by reference.

Alternatively, some manufacturers have elected to use elastomeric films that include two or more layers of material having varying levels of elasticity that are laminated together. In this case, each layer would be formed separately then brought together and laminated. The layers are typically adhered to each other by adhesive bonding, thermal bonding, point bonding, ultrasonic welding or the like. While these laminated elastomeric films may be less expensive in terms of raw materials, additional costs are expended in the formation of separate sheets of material and in conducting the lamination process.

With the foregoing in mind, there is a need or desire for an elastomeric film that exhibits many of the elastic properties such as set, hysteresis and stress relaxation at body temperature of comparable dry-blended and extruded or laminated films.

It is a feature and advantage of the invention to provide an elastomeric film that is less expensive to produce. It also a feature and advantage of the invention to provide an elastomeric film that includes a pure elastomeric polymer and a less expensive and/or less elastic material that is easier to produce and does not involve a difficult and/or detrimental dry blending procedure or an additional lamination process.

It is a further feature and advantage of the invention to provide a composite including an inelastic material such as an extensible nonwoven web and an elastomeric film that is less expensive and easier to produce.

SUMMARY OF THE INVENTION

The present invention is directed to elastomeric films that are easier and less expensive to produce yet exhibit the desirable elasticity properties such as set, hysteresis and stress relaxation at body temperature of comparable dry-blended and extruded or laminated films.

In one embodiment of the present invention, an elastomeric film includes a first layer including a single-site catalyzed ethylene-alpha olefin copolymer co-extruded with a second layer including a styrene copolymer. The single-site catalyzed ethylene-alpha olefin copolymer has a density of about 0.860 to about 0.900 grams per cubic centimeter. The styrene copolymer can be selected from styrene-butadiene-styrene, styrene-isoprene-styrene, styrene-ethylene/butylene-styrene, styrene-ethylene/propylene-styrene, and styrene-(ethylene/propylene)-styrene-(ethylene/propylene). Optionally, the first layer and/or second layer may include filler particles. Additionally, the first layer may be less elastic than the second layer.

In another embodiment of the present invention, an elastomeric film includes a first layer including a single-site catalyzed ethylene alpha olefin copolymer and inorganic filler particles co-extruded with at least a second layer, desirably second and third layers that include a styrene copolymer. The layers are co-extruded such that the first layer is positioned between the second and third layers. The single-site catalyzed ethylene-alpha olefin copolymer has a density of about 0.860 to about 0.900 grams per cubic centimeter. Desirably, the first layer includes about 50 to about 90 percent by volume single-site catalyzed ethylene-alpha olefin copolymer and about 10 to about 50 percent by volume inorganic filler particles. The styrene copolymers of the second and third layers are selected from styrene-butadiene-styrene, styrene-isoprene-styrene, styrene-ethylene/butylene-styrene, styrene-ethylene/propylene-styrene, and styrene(ethylene/propylene)-styrene-(ethylene/propylene). The second and third layers may include the same or different styrene copolymers.

In a further embodiment, an elastomeric film includes at least a first layer, desirably first and third layers that include a single-site catalyzed ethylene alpha olefin copolymer co-extruded with a second layer that includes a styrene copolymer and inorganic filler particles. The layers are co-extruded such that the second layer is positioned between the first and third layers. The single-site catalyzed ethylene-alpha olefin copolymer has a density of about 0.860 to about 0.900 grams per cubic centimeter. The first and third layers may include the same or different single-site catalyzed ethylene-alpha olefin copolymers. The styrene copolymer of the second layer is selected from styrene-butadiene-styrene, styrene-isoprene-styrene, styrene-ethylene/butylene-styrene, styrene-ethylene/propylene-styrene, and styrene-(ethylene/propylene)-styrene-(ethylene/propylene). Desirably, the second layer includes about 50 to about 90 percent by volume styrene copolymer and about 10 to about 50 percent by volume inorganic filler particles.

An extensible laminate including the elastomeric film of the present invention is also disclosed. The extensible laminate includes an extensible nonwoven material and any of the foregoing elastomeric films.

BRIEF DESCRIPTION OF THE DRAWINGS

These and other objects and features of this invention will be better understood from the following detailed description taken in conjunction with the drawings.

DEFINITIONS

The term "extensible" refers to a material that can be stretched without breaking by at least 50% (to at least 150% of its initial unstretched length) in at least one direction, suitably by at least 100% (to at least 200% of its initial unstretched length). For example, an extensible material having an initial unstretched length of 3 inches (7.6 centimeters) may be stretched without breaking to at stretched length of at least 4.5 inches (11.4 centimeters) in at least one direction. The term includes elastic materials as well as materials that stretch but do not significantly retract such as, for example, necked nonwoven materials and inherently extensible nonwoven materials like bonded carded webs.

The terms "elastomeric" or "elastic" refer to a material that can be stretched without breaking by at least 50% (to least 150% of its initial unstretched length) in at least one direction and which, upon release of a stretching, biasing force, will recover at least 30% of its elongation within about one minute.

The term "biaxially extensible" refers to a material that may be stretched by at least about 50% in two directions perpendicular to each other (e.g. stretchable in a machine direction and cross direction, or in a longitudinal direction, front to back, and a lateral direction, side to side). The term includes biaxially extensible laminates such as those disclosed in, for example, U.S. Pat. Nos. 5,114,781 and 5,116,662 to Morman, which are incorporated by reference.

The term "inherently extensible nonwoven material" refers to a nonwoven material that may be stretched by at least 50% in at least one direction without further processing such as necking or creping.

The term "inelastic" refers to both materials that do not stretch by 50% or more and to materials that stretch by that amount but do not retract by more than 30%. Inelastic materials also include materials that do not extend, e.g., which tear when exposed to a stretching force.

The "percent retraction" is determined when an extended or elongated material is relaxed to where the retractive force drops below 10 grams for a 3-inch wide sample (7.6-centimeter). Percent retraction is calculated using the equation ((final length of material after elongation and relaxation minus initial length of material)/(length sample is elongated to minus initial length of material))×100. "Percent permanent set" is 100 minus "percent retraction".

The term "machine direction" for a web, film or laminate refers to the direction in which it was produced. The term "cross direction" for a web, film or laminate refers to the direction perpendicular to the machine direction. Dimensions measured in the cross direction are referred to as "width" dimension, while dimensions measured in the machine direction are referred to as "length" dimensions.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spundbonding processes, air laying processes, coforming processes, and bonded carded web processes. The basis weight of nonwoven fabrics or webs is usually expressed in ounces of material per square yard (osy) or grams of material per square meter (gsm) and the fiber diameters used are usually expressed in microns. (Note that to convert from osy to gsm, multiply osy by 33.91).

"Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well known bonding method, particularly when using bicomponent staple fibers, is through-air bonding.

The term "microfibers" means small diameter fibers typically having an average fiber denier of about 0.005 to 10. Fiber denier is defined as grams per 9000 meters of fiber. For a fiber having a circular cross-section, denier may be calculated as fiber diameter in microns squared, multiplied by the density in grams per cubic centimeter (g/cc) multiplied by 0.00707. For fibers made of the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying that result by 0.00707. Thus, a 15 micron polypropylene has a denier of about 1.42 calculated as ($15^2$×0.89×0.00707=1.415). Outside the United States the unit of measurement is more commonly the "tex" which is defined as grams per kilometer of fiber. Tex may be calculated as denier/9.

The term "spunbond fibers" refers to small diameter fibers which are formed by extruding molten thermoplastic material as filaments from a plurality of fine capillaries of a spinneret having a circular or other configuration, with the diameter of the extruded filaments then being rapidly reduced as in, for example, U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous, are generally smaller than about 1.0 denier, and are generally self-bonding when deposited onto a collecting surface.

As used herein, the term "interfiber bonding" means bonding produced by thermal bonding or entanglement between the individual nonwoven fibers to form a coherent web structure. Fiber entangling is inherent in the meltblown process but may be generated or increased by processes such as, for example, hydraulic entangling or needlepunching. One or more thermal bonding steps are employed in most processes for forming spunbond webs. Alternatively and/or additionally, a bonding agent can be utilized to increase the desired bonding and to maintain structural coherency of the web. For example, powdered bonding agents and chemical solvent bonding may be used.

The term "film" refers to a thermoplastic film made using a film extrusion process, such as a cast film or blown film extrusion process. This term includes films rendered microporous by mixing a polymer with filler, forming a film from the mixture, and stretching the film.

The term "co-extrusion" or "co-extruded" refers to films including two or more layers of thermoplastic material that are extruded simultaneously to form a single, integrated sheet of film without the need for a further attachment or lamination process to bond the layers together.

"Breathable film" or "breathable laminate" refers to a film or laminate having a water vapor transmission rate ("WVTR") of at least about 500 grams/m$^2$/24 hours, using the WVTR Test Procedure described herein.

"Non-breathable film" or "non-breathable laminate" refers to a film or laminate having a water vapor transmission rate ("WVTR") below about 500 grams/m$^2$/24 hours, using the WVTR Test Procedure described herein.

The term "polymer" includes, but is not limited to, homopolymers, copolymers, such as for example, block, graft, random and alternating copolymers, terpolymers, etc. and blends, and modifications thereof. Additionally, the term "polymer" includes thermoplastic and thermoset polymers. Furthermore, unless otherwise specifically limited, the term "polymer" shall include all possible geometrical configurations of the material. These configurations include, but are not limited to, isotactic, syndiotactic and atactic symmetries.

The term "garment" includes pant-like absorbent garments and medical and industrial protective garments. The term "pant-like absorbent garment" includes without limitation diapers, training pants, swim wear, absorbent underpants, baby wipes, adult incontinence products, and feminine hygiene products.

The term "medical protective garment" includes without limitation surgical garments, gowns, aprons, facemasks, and drapes. The term "industrial protective garment" includes without limitation protective uniforms and workwear.

The term "neck" or "neck stretch" interchangeably mean that a fabric, nonwoven web or laminate is extended under conditions reducing its width or its transverse dimension by stretching lengthwise or increasing the length of the fabric. The controlled stretching may take place under cool temperatures, room temperature or greater temperatures and is limited to an increase in the overall dimension in the direction being stretched up to the elongation required to break the fabric, nonwoven web or laminate, which in most cases is about 1.2 to about 1.6 times. Usually, the neck stretching is performed without stretching (lengthening) the individual nonwoven fibers. When relaxed, the fabric, nonwoven web or laminate does not return totally to its original dimensions. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric.

The term "neckable material" or "neckable layer" means any material or layer which can be necked such as a nonwoven, woven, or knitted material, or laminate containing one of them. As used herein, the term "necked material" refers to any material which has been drawn in at least one dimension, (e.g., lengthwise), reducing the transverse dimension, (e.g., width), such that when the drawing force is removed, the material can be pulled back to its original width. The necked material generally has a higher basis weight per unit area than the un-necked material. When the necked material is pulled back to its original width, it should have about the same basis weight as the un-necked material. This differs from stretching/orienting the film layer, during which the film is thinned and the basis weight is reduced. Suitable nonwoven webs for use in the invention are made from inelastic polymer(s).

As used herein, the term "reversibly necked material" refers to a necked material that has been treated while necked to impart memory to the material so that, when a force is applied to extend the material to its pre-necked dimensions, the necked and treated portions will generally recover to their necked dimensions upon termination of the force. One form of treatment is the application of heat. Generally speaking, extension of the reversibly necked material is substantially limited to extension to its pre-necked dimensions. Therefore, unless the material is elastic, extension too far beyond its pre-necked dimensions will result in material failure. A reversibly necked material may include more than one layer, for example, multiple layers of spunbond web, multiple layers of meltblown web, multiple layers of bonded carded web or any other suitable combination or mixtures thereof, as described in U.S. Pat. No. 4,965,122 to Morman, which is incorporated by reference.

The term "percent neckdown" refers to the ratio determined by measuring the difference between the un-necked dimension and the necked dimension of the neckable material and then dividing that difference by the un-necked dimension of the neckable material.

As used herein, the term "sheet" refers to a generally flat structure, which can be composed of a nonwoven material or web, scrim, a woven structure, or a film, such as an elastomeric material.

As used herein, the term "extensible laminate" refers to a material having an elastomeric sheet or film joined to an extensible material at least at two places (e.g., a single-faced extensible laminate). The elastomeric film may be joined to the extensible material at intermittent points or may be completely bonded thereto. The joining is accomplished while the elastomeric film and the extensible material are in juxtaposed configuration. An extensible laminate may include more than two layers. For example, the elastomeric film may have an extensible material joined to both of its sides so that a three-layer extensible laminate is formed having a structure of extensible material/elastomeric film/extensible material (e.g., a two-faced extensible laminate). Additional elastic or elastomeric sheets or films, necked material layers, and/or inherently extensible materials such as bonded carded webs may be added. Other combinations of elastomeric sheets or films and extensible materials may be used, for instance, as indicated in commonly assigned U.S. Pat. Nos. 5,114,781 and 5,116,662 to Morman and 5,336,545 to Morman et al., which are hereby incorporated by reference.

As used herein, the term "single-site catalyzed" refers to polyolefins produced by metallocene-catalyzed polymerization reactions and/or constrained geometry-catalyzed polymerization reactions. Such catalysts are reported in "Metallocene Catalysts Initiate New Era in Polymer Synthesis", Ann M. Thayer, Chemical & Engineering News, Sept. 11, 1995, p. 15.

As used herein, the term "consisting essentially of" does not exclude the presence of additional materials or process steps which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

As used herein, the term "comprising" opens the claim to inclusion of additional materials or process steps other than those recited.

These terms may be defined with additional language in the remaining portions of the specification.

DESCRIPTION OF PREFERRED EMBODIMENTS

The present invention provides an elastomeric film including a first layer co-extruded with at least a second layer. The first layer includes a single-site catalyzed ethylene-alpha olefin copolymer having a density of about 0.860 to about 0.900 grams per cubic centimeter. The second layer includes a styrene copolymer selected from styrene-butadiene-styrene, styrene-isoprene-styrene, styrene-ethylene/butylene-styrene, styrene-ethylene/propylene-styrene, and styrene-(ethylene/propylene)-styrene(ethylene/propylene). Also provided is an extensible laminate including a necked nonwoven web and the elastomeric film.

Figure 1:
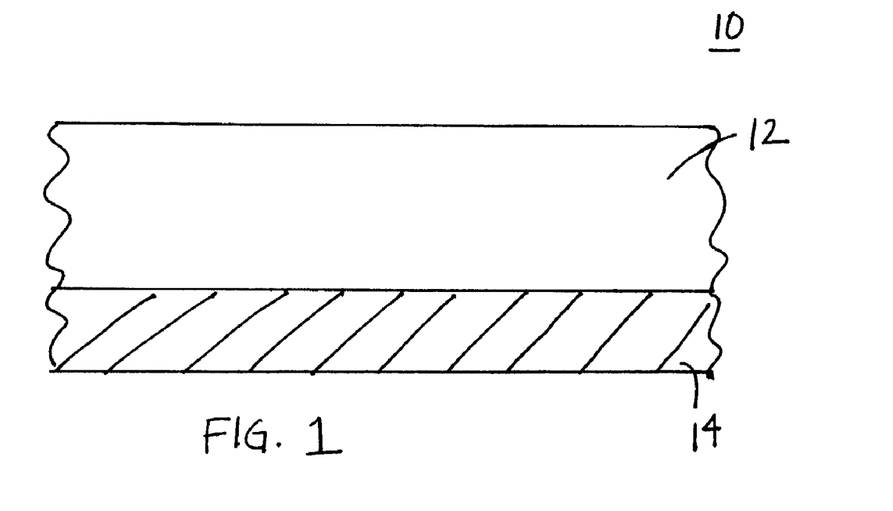
FIG. 1 is a view of an elastomeric film wherein the first layer fills a greater percentage of the volume of the elastomeric film.

FIGS. 1, 2, 3a and 3b illustrate elastomeric films of the present invention. Referring to FIG. 1, an elastomeric film 10 includes a first layer 12 and a second layer 14. Advantageously, the first layer 12 is co-extruded with the second layer 14 to avoid the difficulties of dry blending the single-site catalyzed ethylene-alpha olefin copolymer with the styrene copolymer prior to extrusion. Without wishing to be bound by theory, it is believed that mixing at the high speeds necessary to form a uniformly dispersed mixture of the single-site catalyzed ethylene-alpha olefin copolymer and the styrene copolymer may have a detrimental effect on the segregated phases of the styrene copolymer that enhance the elasticity of the resulting film. For example, dry blending and extrusion of the copolymer resins is believed to negatively impact set, hysteresis and stress relaxation of the elastomeric film. However, by keeping the copolymer resins separate and bringing them together in a die in a co-extruded form, performance of the co-extruded elastomeric film may be enhanced over a blended and extruded film. For example, the set of the co-extruded elastomeric film will likely be dictated by the highly elastic styrene copolymer rather than compromised by the less elastic single-site catalyzed ethylene-alpha olefin copolymer which may occur in dry-blended and extruded films of the same materials. Additionally, because the elasticity properties of the co-extruded elastomeric film are likely controlled by the styrene copolymer and likely not significantly compromised by the single-site catalyzed ethylene-alpha olefin copolymer, it is believed that a lesser amount of the more expensive styrene copolymer is needed to achieve the same set, hysteresis and stress relaxation properties as a comparable blended and extruded elastomeric film of the same copolymer resins. Therefore, the first layer 12 may desirably constitute a greater percentage by volume of the elastomeric film 10. Thus, the co-extruded elastomeric film of the present invention is believed to be more economical and less difficult to produce than comparable dry-blended and extruded elastomeric films.

Desirably, the first layer 12 of the elastomeric film 10 constitutes about 10 to about 80 percent by volume of the total elastomeric film 10. More desirably, the first layer 12 of the elastomeric film 10 constitutes about 30 to about 70 percent by volume of the total elastomeric film. Most desirably, the first layer 12 of the elastomeric film 10 constitutes greater than about 50 percent by volume of the total elastomeric film 10.

The first layer 12 includes a single-site catalyzed ethylene-alpha olefin copolymer having a density of about 0.860 to about 0.900 grams per cubic centimeter. Suitable single-site catalyzed ethylene-alpha olefin copolymers include about 70 to about 90 percent by weight ethylene and about 10 to about 30 percent by weight of a $C_3$-$C_{12}$ alpha olefin co-monomer. More suitably, the single-site catalyzed ethylene-alpha olefin copolymer includes about 75 to about 90 percent by weight ethylene and about 10 to about 25 percent by weight of a $C_3$-$C_{12}$ alpha olefin co-monomer. Desirably, the single-site catalyzed ethylene-alpha olefin copolymers are selected from the copolymers of ethylene and 1-butene, copolymers of ethylene and 1-hexene, copolymers of ethylene and 1-octene, and combinations thereof.

The term "single-site catalyzed ethylene-alpha olefin copolymer" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Metallocene process catalysts include bis(n-butylcyclopentadienyl) titanium dichloride, bis(n-butylcyclopentadienyl) zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-fluorenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to Dow Chemical Company. Such compounds are also discussed in U.S. Pat. No. 5,064,802 to Stevens et al. and also assigned to Dow.

Ethylene-alpha olefin copolymers made using single-site catalysts such as metallocene catalysts have a very narrow molecular weight range. As a function of the metallocene structures it is possible to control molar mass, molar mass distribution, stereochemistry, end groups, co-monomer incorporation, long- and short-chain branching, morphology, polymer compatibility, and elastomer properties. Polydispersity numbers (Mw/Mn) of below 4 and even below 2 are possible for metallocene-produced copolymers. These copolymers have a controlled short chain branching distribution compared to otherwise similar Ziegler-Natta produced type copolymers. It is also possible using a metallocene catalyst system to control the isotacticity of the copolymer quite closely. In general, single-site catalyzed ethylene-alpha olefin copolymers having higher densities tend to be less elastic than single-site ethylene-alpha copolymers having lower densities.

Commercial production of single-site catalyzed ethylene-alpha olefin copolymers is somewhat limited but growing. Such copolymers are available from Exxon-Mobil Chemical Company of Houston, Tex. under the registered trademarks EXACT and EXCEED. Dow Chemical Company of Midland, Mich. has copolymers commercially available under the registered trademarks ENGAGE and AFFINITY. Single-site catalyzed ethylene-alpha olefin copolymers suitable for use in the present invention include, for example, ENGAGE EG8200 and AFFINITY XUS58380.01L.

The second layer 14 includes a styrene copolymer, for example, a polymer selected from styrene-butadiene-styrene, styrene-isoprene-styrene, styrene-ethylene/butylene-styrene, styrene-ethylene/propylene-styrene, styrene(ethylene/propylene)-styrene-(ethylene/propylene), and combinations thereof. Such styrene copolymers are typically highly elastic and substantially control the overall elasticity of the co-extruded elastomeric film. Styrene copolymers suitable for use in the present invention are available from KRATON Polymers of Houston, Tex. under the registered trademark KRATRON. One such copolymer may be, for example, KRATON G-1657. Suitable KRATON copolymer blends include, for example, KRATON G-2755 and KRATON G-2760.

Advantageously, because a lesser amount of highly elastic styrene copolymer is needed to achieve elastic properties similar to those of comparable dry-blended and extruded or laminated elastomeric films, the second layer 14 may constitute about 20 to about 90 percent by volume of the elastomeric film 10. More suitably, the second layer 14 may constitute about 30 to about 70 percent by volume of the elastomeric film 10. Most suitably, the second layer 14 may constitute less than about 50 percent by volume of the elastomeric film 10.

Figure 2:
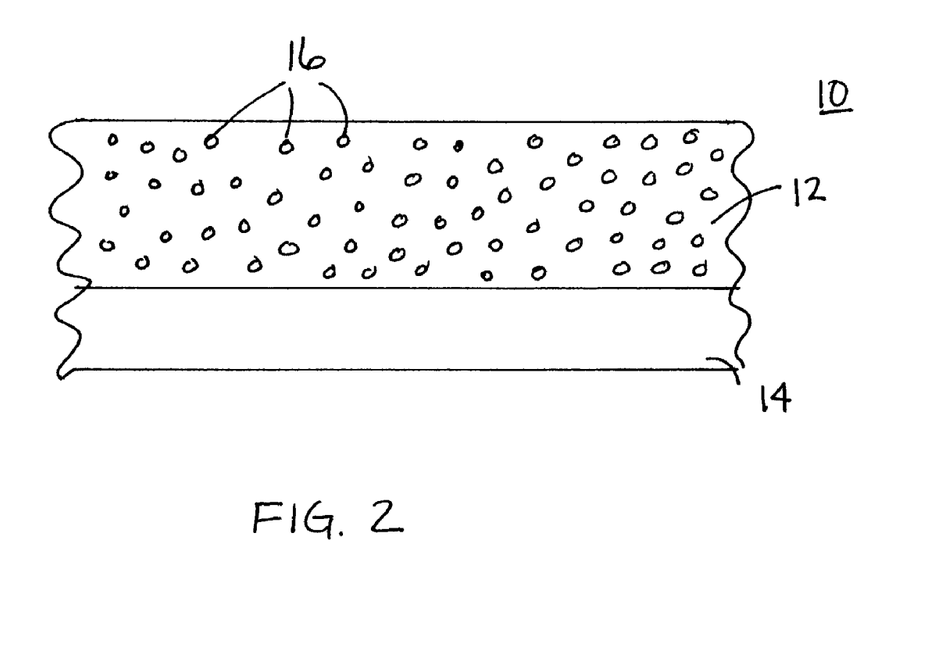
FIG. 2 is an illustration of an elastomeric film wherein the first layer includes filler particles.

Referring to FIG. 2, the first layer 12 may include filler particles 16. Alternatively or additionally, the second layer 14 may include filler particles 16 (not shown). Filler particles are typically used to reduce the costs associated with producing elastomeric films since a lesser amount of copolymer is utilized. Advantageously, the filler particles 16 are blended with the single-site catalyzed ethylene-alpha olefin copolymer to form a filled single-site catalyzed ethylene-alpha olefin copolymer that is co-extruded with the styrene copolymer. The filler particles are desirably provided in a polymer concentrate or masterbatch to facilitate better dispersion. The masterbatch or "letdown" polymer may be the same single-site catalyzed polymer or a different polymer. Alternatively or additionally, filler particles 16 may be blended with the styrene copolymer to form a filled styrene copolymer that is co-extruded with the single-site catalyzed ethylene-alpha olefin copolymer. The filler particles are desirably provided in a letdown polymer that may be the same styrene copolymer or a different styrene copolymer.

Films including filler particles typically include a plurality of voids within the matrix surrounded by relatively thin microporous membranes defining tortuous paths, and one or more of the filler particles in each void. The voids are formed when the film is stretched, thereby creating a breathable, microporous film, wherein the microporous membranes between the voids readily permit molecular diffusion of water vapor from a first surface to a second surface of the film. Alternatively, some or all of the micropores can pass through the film, or can be interconnected to provide through-passages. However, if the film is not stretched during production the film does not develop the microporosity, or the consequent breathability, normally associated with filled films. Instead, the filler particles are compounded with the polymer matrix as a cost-effective means of adding stiffness to the film. The resulting film is therefore considered non-breathable, with a water-vapor transmission rate (WVTR) of less than about 500 grams/m$^2$/24 hours.

The amount of filler particles 16 included in the filled copolymer or copolymers affects, in part, the level of elasticity of the film layers and may render one layer less elastic than the other layer or may render one layer substantially inelastic. For example, a first layer 12 including filler particles 16 may be less elastic than a second layer 14. Advantageously, the first layer 12 may include about 50 to about 90 percent by volume single-site catalyzed ethylene-alpha olefin copolymer and about 10 to about 50 percent by volume filler particles 16. More advantageously, the first layer 12 may include about 60 to about 80 percent by volume single-site catalyzed ethylene-alpha olefin copolymer and about 20 to about 40 percent by volume filler particles 16. Alternatively or additionally, the second layer 14 may include about 50 to about 90 percent by volume styrene copolymer and about 10 to about 50 percent by volume filler particles 16. Desirably, the second layer 14 may include about 60 to about 80 percent by volume styrene copolymer and about 20 to about 40 percent by volume filler particles 16.

The filler particles 16 may include any suitable organic or inorganic material. Generally, the filler particles should have a mean particle diameter of about 0.1 to about 8.0 microns, desirably about 0.5 to about 5.0 microns, and more desirably about 0.8 to about 2.0 microns. Suitable inorganic filler particles include without limitation calcium carbonate, non-swellable clays, silica, alumina, barium sulfate, sodium carbonate, talc, magnesium sulfate, titanium dioxide, zeolites, aluminum sulfate, diatomaceous earth, magnesium carbonate, barium carbonate, kaolin, mica, carbon, calcium oxide, magnesium oxide, aluminum hydroxide. Suitable organic filler particles include polymer particles or beads. Calcium carbonate is the presently desired filler particle.

The filler particles 16 may be coated with a minor quantity (e.g., up to about 2 percent by weight) of a fatty acid or other material to ease their dispersion in the single-site catalyzed ethylene-alpha olefin copolymer. Suitable fatty acids include without limitation stearic acid, or a larger chain fatty acid such as behenic acid.

Figure 3A:
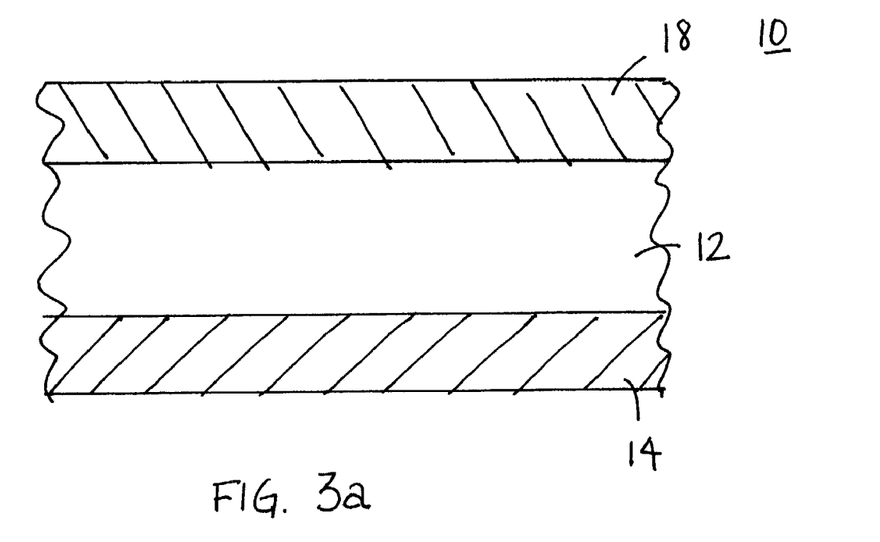
FIGS. 3a and 3b are views of an elastomeric film including three co-extruded layers.

In another embodiment, as shown in FIG. 3a, an elastomeric film 10 includes a first layer 12, a second layer 14 and a third layer 18. Suitably, the three layers are co-extruded such that the first layer 12 is extruded between the second layer 14 and the third layer 18. The first layer 12 includes a single-site catalyzed ethylene-alpha olefin copolymer having a density of about 0.860 to about 0.900 grams per cubic centimeter. The second layer 14 and the third layer 18 include a styrene copolymer selected from styrene-butadiene-styrene, styrene-isoprene-styrene, styrene-ethylene/butylene-styrene, styrene-ethylene/propylene-styrene, and styrene-(ethylene/propylene)-styrene(ethylene/propylene). The second layer 14 and the third layer 18 may include the same styrene copolymer. Alternatively, the third layer 18 may include a different styrene copolymer than the second layer 14. Optionally, the first layer 12 may include filler particles 16 (not shown) as defined above.

Figure 3B:
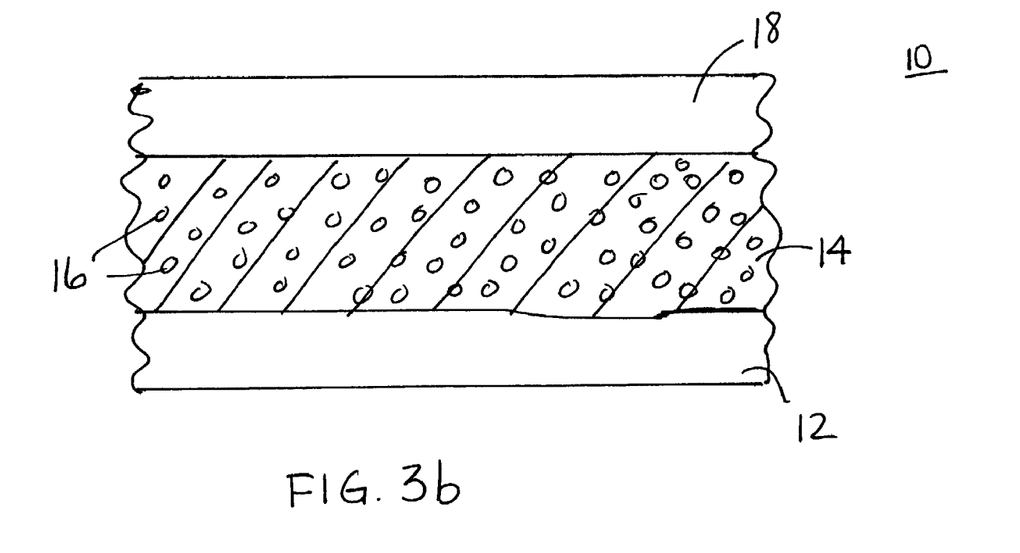

In a further embodiment, shown in FIG. 3b, an elastomeric film 10 includes a first layer 12, a second layer 14 and a third layer 18. Suitably, the three layers are co-extruded such that the second layer 14 is extruded between the first layer 12 and the third layer 18. The first layer 12 and the third layer 18 include a single-site catalyzed ethylene-alpha olefin copolymer having a density of about 0.860 to about 0.900 grams per cubic centimeter. The first layer 12 and the third layer 18 may include the same single-site catalyzed ethylene-alpha olefin copolymer. Alternatively, the third layer 18 may include a different single-site catalyzed ethylene-alpha olefin copolymer than the first layer 12. The second layer 14 includes a styrene copolymer selected from styrene-butadiene-styrene, styrene-isoprene-styrene, styrene-ethylene/butylene-styrene, styrene-ethylene/propylene-styrene, and styrene-(ethylene/propylene)-styrene-(ethylene/propylene). Optionally, the second layer 14 may include filler particles 16 as defined above.

Although the elastomeric films of the present invention are depicted in FIGS. 1, 2, 3a and 3b as including only two or three layers, it is to be understood that the elastomeric film may include additional layers of elastomeric, less elastic and/or non-elastic material.

Figure 4:
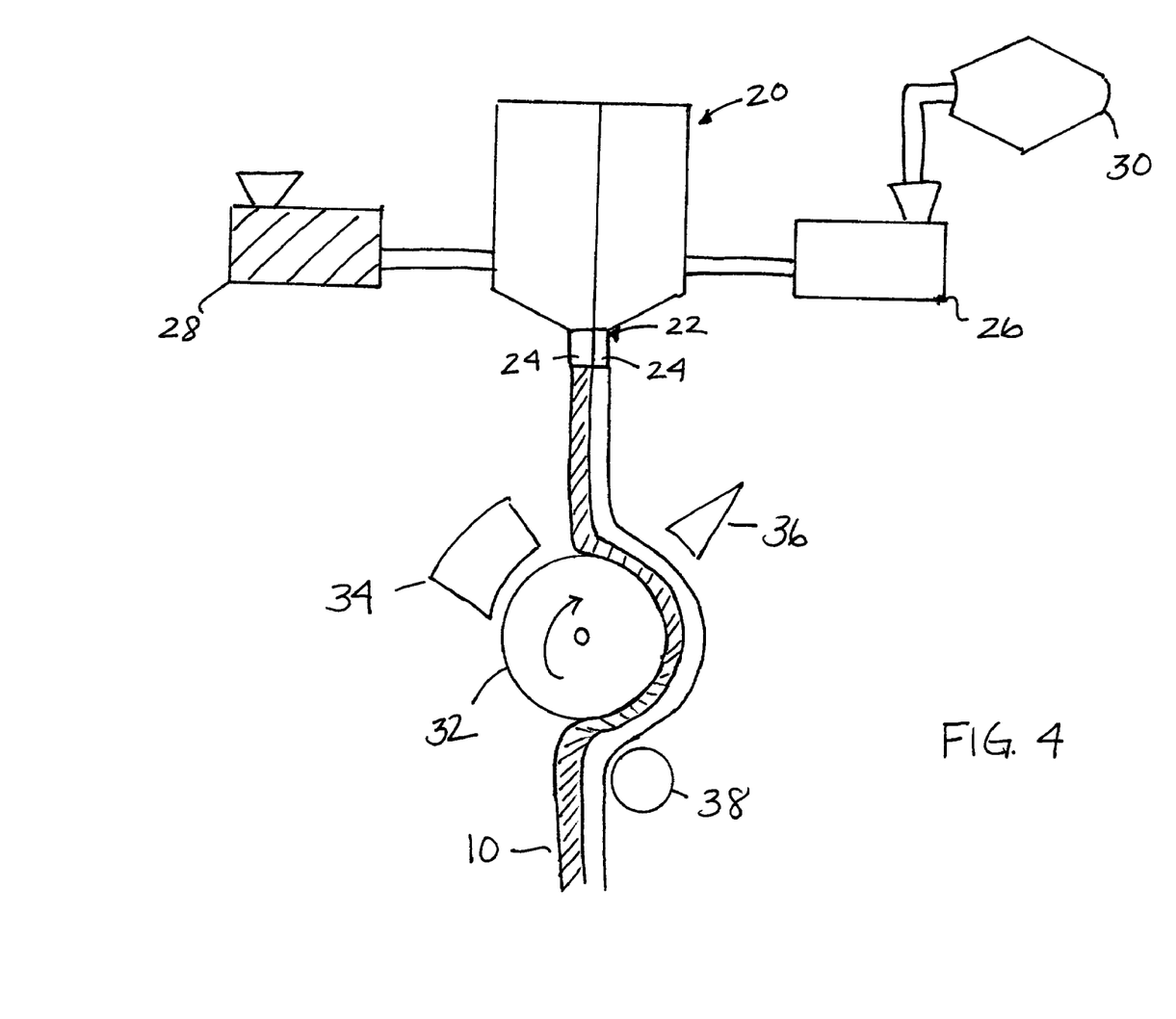
FIG. 4 schematically illustrates a process for making an elastomeric film.

Referring to FIG. 4, a process for making the elastomeric film of the present invention is disclosed. The elastomeric film 10 is formed from a film co-extrusion apparatus 20 that includes a die 22 having a least two extrusion ports 24. The film co-extrusion apparatus 20 may be a cast or blown unit which could be in-line with another forming process or off-line. As shown in FIG. 4, the co-extrusion apparatus 20 includes a first extruder 26 containing a single-site ethylene-alpha olefin copolymer and a second extruder 28 containing a styrene copolymer. Optionally, the co-extrusion apparatus 20 could include additional extruders for forming additional layers in the co-extruded elastomeric film. The co-extrusion apparatus 20 may also include a mixing apparatus 30 wherein the single-site catalyzed ethylene-alpha olefin copolymer is blended with filler particles prior to extrusion. The elastomeric film 10 is co-extruded onto a chill roller 32, which cools the elastomeric film 10. A vacuum box 34 adjacent the chill roller 32 creates a vacuum on the surface of the chill roller to help maintain the film close to the surface of the chill roller. Air knives or electrostatic pinners 36 also urge the elastomeric film 10 against the surface of the chill roller 32. The elastomeric film 10 is passed through a nip between the chill roller 32 and a nip roll 38 to set the layers and remove the cooled film from the chill roller 32. The elastomeric film 10 may be carried to another in-line process or may be wound on a take-up roll (not shown) for off-line use. Optionally, if the elastomeric film 10 includes filler particles, it may be stretched prior to lamination to an extensible material in order to render the elastomeric film and the resulting extensible laminate breathable.

Figure 5:
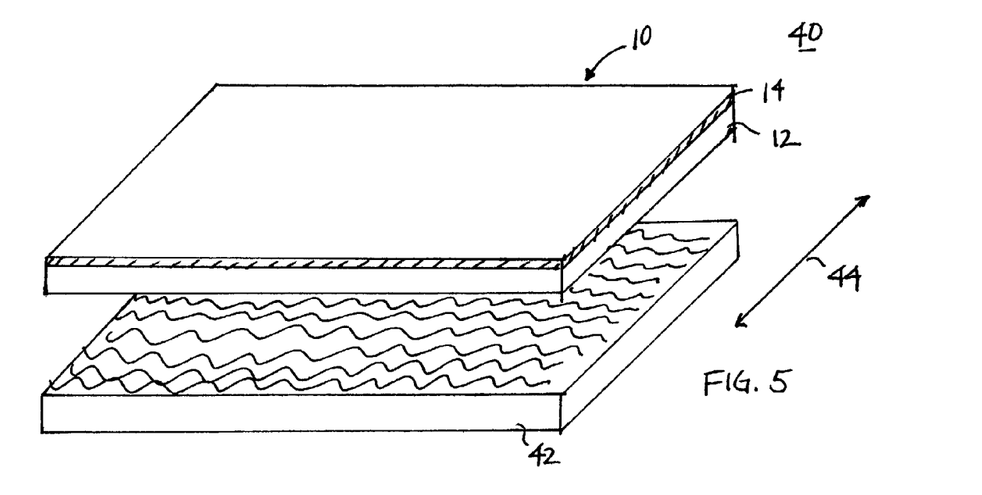
FIG. 5 is a view of an extensible laminate including an elastomeric film.

The co-extruded elastomeric film 10 may be laminated to an extensible material to form an elastic composite. Referring to FIG. 5, an extensible laminate 40 includes an extensible nonwoven web 42 and an elastomeric film 10 having a first layer 12 co-extruded with a second layer 14. The first layer 12 includes a single-site catalyzed ethylene-alpha olefin copolymer having a density of about 0.860 to about 0.900 grams per cubic centimeter. The second layer 14 includes a styrene copolymer selected from styrene-butadiene-styrene, styrene-isoprene-styrene, styrene-ethylene/butylene-styrene, styrene-ethylene/propylene-styrene, and styrene-(ethylene/propylene)-styrene-(ethylene/propylene). Optionally, the first and/or second layer may include filler particles 16 (not shown). Any elastomeric film 10 as disclosed above may be laminated to the extensible nonwoven web 42.

The extensible laminate 40 is extensible in the cross direction 44 due to the influence of the extensible nonwoven web 42. When a cross-directional extension force is removed, the extensible laminate 40 will return substantially to its manufactured configuration due to the influence of the elastomeric film 10. Such extensible laminates are suitable for use in absorbent articles, garments, pads, diapers, training pants, swimwear, adult incontinence products, feminine care products, medical protective garments, and industrial protective garments.

Suitably, the extensible nonwoven material 42 may be an inherently extensible nonwoven material such as, for example, an oriented bonded carded web or a crimped bicomponent spunbond material as disclosed in commonly assigned U.S. Pat. No. 5,418,045 issued to Pike et al.

Other suitable extensible nonwoven materials include biaxially extensible nonwoven materials such as neck stretched/creped spunbond. The machine direction and cross direction extensible nonwoven material can be provided by stretching a fibrous nonwoven material in a machine direction to cause necking (and extensibility) in the cross direction. Alternatively, the nonwoven material may be a very loose collection of fibers bonded discontinuously in the cross direction such that the material can be stretched in the cross direction. The same material with the imparted cross direction extensibility may be crimped or creped in the machine direction to cause machine direction extensibility.

The extensible nonwoven material 42 may also be a necked nonwoven material such as, for example, a necked spunbond web, meltblown web or bonded carded web. If the necked nonwoven material is a web of meltblown fibers, it may include meltblown microfibers. The necked nonwoven material may be made from any material that can be necked. The necked material may also be treated while necked so that, after treatment, upon application of a force to extend the necked material to its pre-necked dimensions, the material recovers generally to its necked dimensions upon termination of the force (e.g., a reversibly necked material). A method of treatment is the application of heat. Certain polymers such as, for example, polyolefins, polyesters and polyamides may be heat treated under suitable conditions to impart such memory. Exemplary polyolefins include one or more of polyethylene, polypropylene, polybutene, ethylene copolymers, propylene copolymers and butene copolymers. Polypropylenes that have been found useful include, for example, polypropylene available from the Himont Corporation of Wilmington, Del. under the trade designation PF-304, polypropylene available from the Exxon-Mobil Chemical Company under the registered trademark ESCORENE PD-3445, and polypropylene available from the Shell Chemical Company of Houston, Tex. under the trade designation DX 5A09. Polyethylenes may also be used, including ASPUN 6811A and 2553 linear low density polyethylenes from the Dow Chemical Company, as well as various high density polyethylenes. Chemical characteristics of these materials are available from their respective manufacturers.

In one embodiment of the present invention, the necked nonwoven material may be a multilayer material having, for example, at least one layer of spunbond web joined to at least one layer of meltblown web, bonded carded web, film or other suitable material. For example, the necked nonwoven material may be a multilayer material having a first layer of spunbond polyolefin having a basis weight from about 0.2 to about 8 ounces per square yard (osy) (about 6.8 to about 271.3 grams per meter (gsm)), a layer of meltblown polyolefin having a basis weight from about 0.1 to about 4 osy (about 3.4 to about 113.4 gsm), and a second layer of spunbond polyolefin having a basis weight of about 0.2 to about 8 osy (about 6.8 to about 271.3 gsm).

Alternatively, the necked nonwoven material may be single layer of material such as, for example, a spunbond web having a basis weight of from about 0.2 to about 10 osy (about 6.8 to about 339.1 gsm) or a meltblown web having a basis weight of from about 0.2 to about 8 osy (about 6.8 to about 271.3 gsm). Suitably, the necked nonwoven material may have a percent neckdown of from about 15% to about 75%. Desirably, the necked nonwoven material 42 may have a percent neckdown of from about 25% to about 70%.

The necked nonwoven material may also include a composite material made of a mixture of two or more different fibers or a mixture of fibers and particulates. Such mixtures may be formed by adding fibers and/or particulates to a gas stream in which meltblown fibers are carried so that an intimate entangled commingling of meltblown fibers and other materials (e.g., wood pulp, staple fibers or particulates such as, for example, superabsorbent materials) occurs prior to collection of the fibers upon a collecting device to form a coherent web of randomly dispersed meltblown fibers and other materials such as disclosed in U.S. Pat. No. 4,100,324 to Anderson et al., which is incorporated by reference.

The fibers of the necked nonwoven material may be joined by interfiber bonding using one or more of the bonding processes described in the foregoing "DEFINITION" of interfiber bonding.

Figure 7:
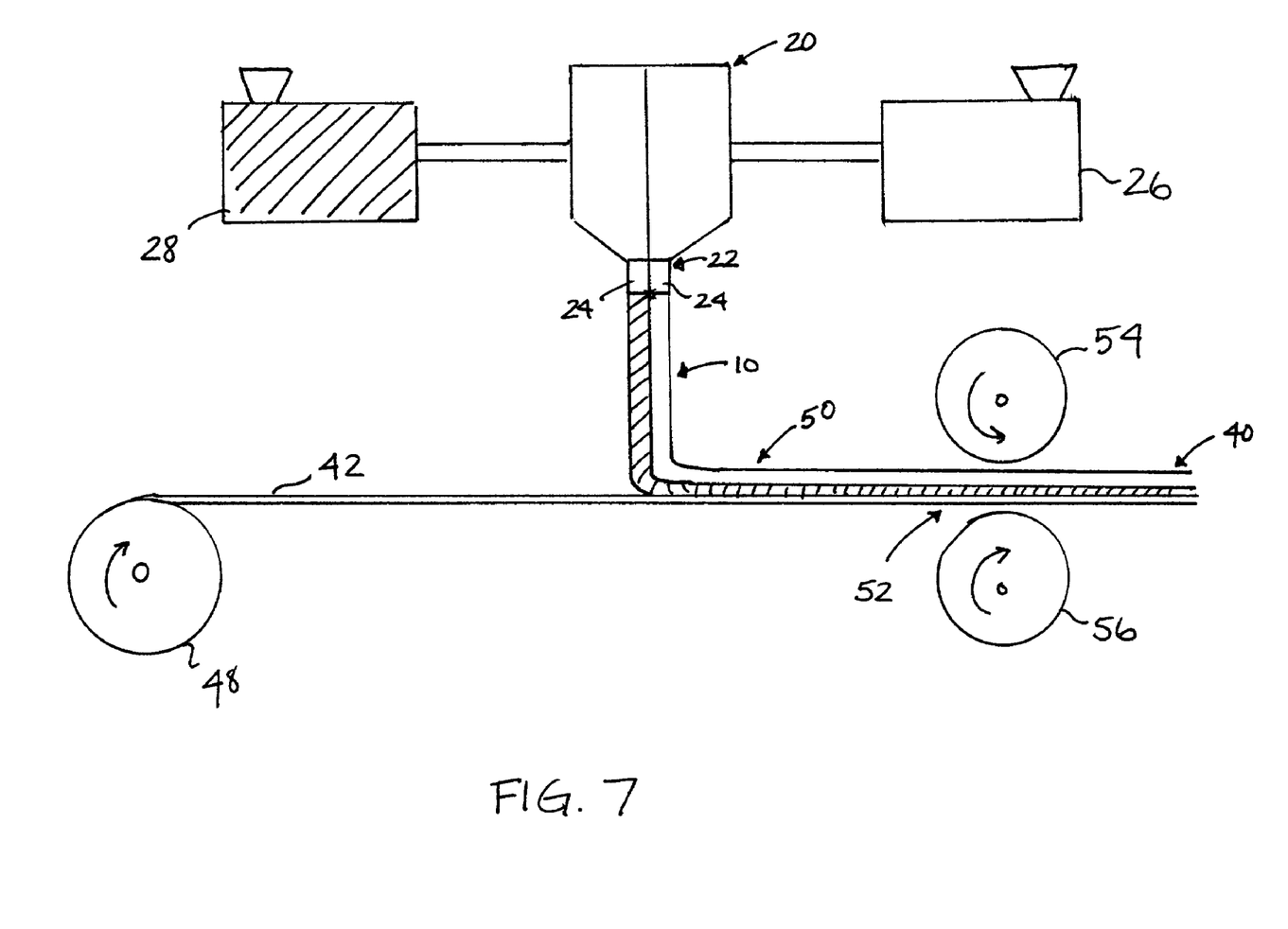
FIG. 7 schematically illustrates a process for laminating a molten co-extruded elastomeric film to an extensible nonwoven material to form an extensible laminate.
Figure 8:
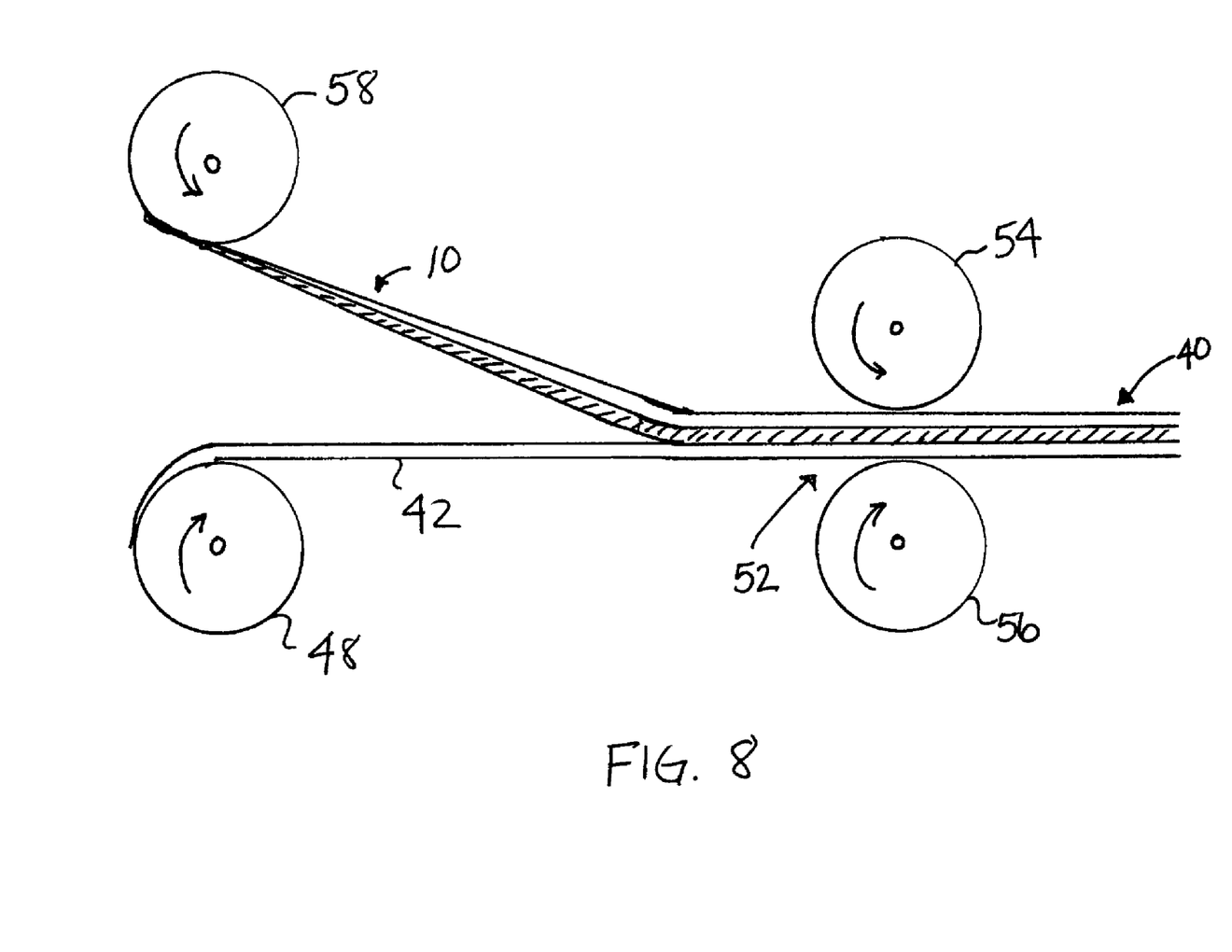
FIG. 8 schematically illustrates a process for laminating a co-extruded elastomeric film to an extensible nonwoven material to form an extensible laminate.

The elastomeric film 10 may be laminated to the extensible nonwoven web 42 by any suitable technique known in the art such as, but not limited to, adhesive bonding, point bonding, thermal bonding, ultrasonic welding, or a combination thereof. For example, referring to FIG. 7, a web of extensible nonwoven material 42 is unrolled from a supply roll 48 and passed under a co-extrusion apparatus 20. The elastomeric film 10 is co-extruded onto the extensible nonwoven web 42 to form a coated web 50. The coated web 50 is passed through a nip 52 between a first nip roll 54 and a second nip roll 56 to produce an extensible laminate 40. Alternatively, as shown in FIG. 8, the co-extruded elastomeric film 10 is unrolled from supply roll 58 in a juxtaposed configuration with the extensible nonwoven web 42 as it is unrolled from supply roll 48. The juxtaposed webs are passed through a nip 52 between a first nip roll 54 and a second nip roll 56 to form an extensible laminate 40. Nip roll 54 and nip roll 56 may be heated to thermally laminate the co-extruded elastomeric film 10 to the extensible nonwoven web 42. Alternatively, nip roll 56 may be patterned and nip roll 54 may be smooth such that when the juxtaposed extensible nonwoven web 42 and co-extruded elastomeric film 10 pass through nip 52 the co-extruded elastomeric film 10 is point bonded to the extensible nonwoven web 42. The patterned nip roll 56 may be heated or may be an ultrasonic bonding horn such that thermal point bonds are formed between the extensible nonwoven web 42 and the co-extruded elastomeric film 10.

Figure 6:
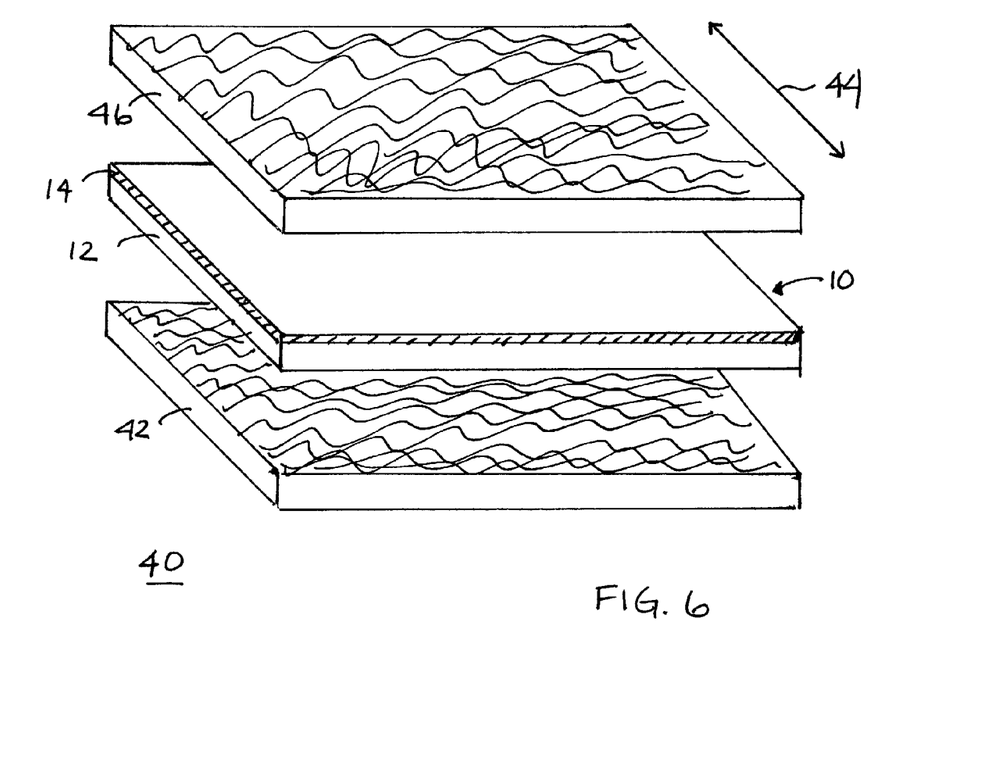
FIG. 6 is an illustration of an extensible laminate including at least one extensible nonwoven web and at least one elastomeric film.

Optionally, the extensible laminate 40 may include additional layers of nonwoven material and/or elastomeric film material. For example, as shown in FIG. 6, a extensible laminate 40 includes a first sheet of extensible nonwoven material 42, a sheet of an elastomeric film 10 including a first layer 12 co-extruded with a second layer 14, and a second sheet of an extensible nonwoven material 46. The first layer 12 includes a single-site catalyzed ethylene-alpha olefin copolymer having a density of about 0.860 to about 0.900 grams per cubic centimeter. The second layer 14 includes a styrene copolymer selected from styrene-butadiene-styrene, styrene-isoprene-styrene, styrene-ethylene/butylene-styrene, styrene-ethylene/propylene-styrene, and styrene(ethylene/propylene)-styrene-(ethylene/propylene).

The first sheet of extensible nonwoven material 42 and the second sheet of extensible nonwoven material 46 may be the same material or may be different materials. For example, the first sheet 42 may be a spunbond web while the second sheet 46 may be a spunbond web, a meltblown web, a bonded carded web, or a multilayer composite thereof. Furthermore, the first sheet 42 may be an extensible nonwoven material having one basis weight and the second sheet 46 may be an extensible nonwoven material having the same or a different basis weight.

The elastomeric film of the present invention may also be used to form biaxially extensible laminates such as by the processes disclosed in U.S. Pat. Nos. 5,114,781 and 5,116,662 to Morman, which are hereby incorporated by reference.

Water Vapor Transmission Rate Test

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer than calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:

WVTR: The calculation of the WVTR uses the formula:

$$WVTR = F\rho_{sat}(T)RH / Ap_{sat}(T)(1-RH))$$

where:

F=The flow of water vapor in cc/min., $\rho_{sat}(T)$=The density of water in saturated air at temperature T, RH=The relative humidity at specified locations in the cell, A=The cross sectional area of the cell, and, $P_{sat}(T)$=The saturation vapor pressure of water vapor at temperature T.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An extensible laminate comprising:
   an extensible nonwoven web; and
   an elastomeric film including a first layer co-extruded with a second layer, wherein the first layer is less elastic than the second layer,
   the first layer having a Water Vapor Transmission Rate less than about 500 grams/m²/24 hours as measured according to INDA standard test method IST-70.4-99 and including a single-site catalyzed ethylene-alpha olefin copolymer having a density of about 0.860 to about 0.900 grams per cubic centimeter and inorganic filler particles, wherein the first layer includes about 50 to about 90 percent by volume of a single-site catalyzed ethylene-alpha olefin copolymer and about 10 percent to about 50 percent by volume inorganic filler particles,
   the second layer including a styrene copolymer selected from styrene-butadiene-styrene, styrene-isoprene-styrene, styrene-ethylene/butylene-styrene, styrene-ethylene/propylene-styrene, styrene-(ethylene/propylene)-styrene-(ethylene/propylene), or combinations thereof, wherein the second layer comprises about 55 percent to about 80 percent by volume of the elastomeric film.

2. The extensible laminate of claim 1, wherein the first layer is inelastic.

3. The extensible laminate of claim 1, wherein the single-site catalyzed ethylene-alpha olefin copolymer includes about 70 to about 90 weight percent ethylene and about 10 to about 30 weight percent of a $C_3$-$C_{12}$ alpha olefin co-monomer.

4. The extensible laminate of claim 1, wherein the filler particles comprise a material selected from calcium carbonate, non-swellable clay, silica, alumina, barium sulfate, sodium carbonate, talc, magnesium sulfate, titanium dioxide, barium carbonate, kaolin, mica, carbon, calcium oxide, magnesium oxide, aluminum oxide, or combinations thereof.

5. An extensible laminate comprising:
   at least one extensible nonwoven web; and
   at least one elastomeric film including a first layer co-extruded with a second layer and a third layer,
   the first layer having a Water Vapor Transmission Rate of less than about 500 g/m²/24 hours as measured according to INDA standard test method IST-70.4-99 and including a single-site catalyzed ethylene-alpha olefin copolymer having a density of about 0.860 to about 0.900 grams per cubic centimeter and inorganic filler particles, wherein the first layer includes about 50 percent to about 90 percent by volume of single-site catalyzed ethylene-alpha olefin copolymer and about 10 percent to about 50 percent by volume inorganic filler particles,
   the second layer including about 50 percent to about 90 percent by volume of a styrene copolymer selected from styrene-butadiene-styrene, styrene-isoprene-styrene, styrene-ethylene/butylene-styrene, styrene-ethylene/propylene-styrene, styrene-(ethylene/propylene)-styrene-(ethylene/propylene), or combinations thereof,
   the third layer including a single-site catalyzed ethylene-alpha olefin copolymer having a density of about 0.860 to about 0.900 grams per cubic centimeter, and
   wherein the second layer is coextruded between the first layer and the third layer of the elastomeric film.

6. The extensible laminate of claim 1, wherein the elastomeric film further comprises a third layer co-extruded with the second layer, the third layer including a single-site catalyzed ethylene-alpha olefin copolymer having a density of about 0.860 to about 0.900 grams per cubic centimeter.

7. The extensible laminate of claim 6, wherein the second layer is coextruded between the first layer and the third layer of the elastomeric film.

8. The extensible laminate of claim 1, further comprising a second extensible nonwoven web.

9. The extensible laminate of claim 1, wherein the nonwoven web is necked.

10. The extensible laminate of claim 9, wherein the necked nonwoven web comprises a percent neckdown of from about 15% to about 75%.

11. The extensible laminate of claim 9, wherein the necked nonwoven web comprises a percent neckdown of from about 25% to about 70%.

12. The extensible laminate of claim 9, wherein the necked nonwoven web comprises a basis weight of from about 0.2 to about 10 ounces per square yard.

13. The extensible laminate of claim 9, wherein the necked nonwoven web comprises a basis weight of from about 0.2 to about 8 ounces per square yard.

14. The extensible laminate of claim 5, wherein the nonwoven web is necked.

15. The extensible laminate of claim 14, wherein the necked nonwoven web comprises a percent neckdown of from about 15% to about 75%.

16. The extensible laminate of claim 14, wherein the necked nonwoven web comprises a percent neckdown of from about 25% to about 70%.

17. The extensible laminate of claim 14, wherein the necked nonwoven web comprises a basis weight of from about 0.2 to about 10 ounces per square yard.

18. The extensible laminate of claim 14, wherein the necked nonwoven web comprises a basis weight of from about 0.2 to about 8 ounces per square yard.

19. The extensible laminate of claim 8, wherein the second nonwoven web is necked.

20. The extensible laminate of claim 1, wherein the elastomeric film is not stretched prior to or during formation of the laminate to impart breathability.

21. The extensible laminate of claim 5, wherein the third layer further includes inorganic filler particles, wherein the third layer comprises about 50 percent to about 90 percent by volume of single-site catalyzed ethylene-alpha olefin copolymer and about 10 percent to about 50 percent by volume inorganic filler particles.

22. The extensible laminate of claim 5, wherein the single-site catalyzed ethylene-alpha olefin copolymers include about 70 to about 90 weight percent ethylene and about 10 to about 30 weight percent of a $C_3$-$C_{12}$ alpha olefin co-monomer.

23. The extensible laminate of claim 5, wherein the filler particles comprise a material selected from calcium carbonate, non-swellable clay, silica, alumina, barium sulfate, sodium carbonate, talc, magnesium sulfate, titanium dioxide, barium carbonate, kaolin, mica, carbon, calcium oxide, magnesium oxide, aluminum oxide, or combinations thereof.

24. The extensible laminate of claim 5, further comprising a second extensible nonwoven web.

25. The extensible laminate of claim 5, wherein the elastomeric film is not stretched prior to or during formation of the laminate to impart breathability.

26. An extensible laminate comprising:
at least one extensible nonwoven web; and
at least one elastomeric film including a first layer coextruded with a second layer and a third layer,
the first layer including a single-site catalyzed ethylene-alpha olefin copolymer having a density of about 0.860 to about 0.900 grams per cubic centimeter,
the second layer including about 50 percent to about 90 percent by volume of a styrene copolymer selected from styrene-butadiene-styrene, styrene-isoprene-styrene, styrene-ethylene/butylene-styrene, styrene-ethylene/propylene-styrene, styrene-(ethylene/propylene)-styrene-(ethylene/propylene), or combinations thereof and about 10 percent to about 50 percent by volume inorganic filler particles,
the third layer including a single-site catalyzed ethylene-alpha olefin copolymer having a density of about 0.860 to about 0.900 grams per cubic centimeter,
wherein the second layer is coextruded between the first layer and the third layer of the elastomeric film.

27. The extensible laminate of claim 26, wherein the first layer further includes inorganic filler particles, wherein the third layer comprises about 50 percent to about 90 percent by volume of single-site catalyzed ethylene-alpha olefin copolymer and about 10 percent to about 50 percent by volume inorganic filler particles.

28. The extensible laminate of claim 26, wherein the first layer and the third layer further include inorganic filler particles, wherein the first layer and the third layer comprises about 50 percent to about 90 percent by volume of single-site catalyzed ethylene-alpha olefin copolymer and about 10 percent to about 50 percent by volume inorganic filler particles.

29. The extensible laminate of claim 26, wherein the elastomeric film is not stretched prior to or during formation of the laminate to impart breathability.

* * * * *